(12) United States Patent
Chu

(10) Patent No.: US 6,284,194 B1
(45) Date of Patent: Sep. 4, 2001

(54) ANALYTICAL ASSAY DEVICE AND METHODS USING SURFACTANT TREATED MEMBRANES TO INCREASE ASSAY SENSITIVITY

(76) Inventor: Albert E. Chu, 140 Roblar Ave., Hillsborough, CA (US) 94010

( * ) Notice: Subject to any disclaimer, the term of this patent is extended or adjusted under 35 U.S.C. 154(b) by 0 days.

(21) Appl. No.: 09/038,796

(22) Filed: Mar. 11, 1998

(51) Int. Cl.[7] .................................................. G01N 33/553
(52) U.S. Cl. .............................. 422/55; 422/56; 422/57; 422/58; 422/60; 435/5; 435/4; 435/6; 435/7.1; 435/7.92; 435/805; 435/810; 436/514; 436/516; 436/518; 436/528; 436/808
(58) Field of Search .................... 422/55–58, 60; 435/5, 6, 4, 7.1, 7.92, 805, 810; 436/514, 516, 518, 528, 808

(56) References Cited

U.S. PATENT DOCUMENTS

| | | |
|---|---|---|
| 4,366,241 | 12/1982 | Tom et al. . |
| 4,632,901 | 12/1986 | Valkris et al. . |
| 4,640,898 | 2/1987 | Halfman . |
| 4,774,192 | 9/1988 | Terminiello et al. . |
| 4,810,630 | 3/1989 | Craig et al. . |
| 4,818,677 | 4/1989 | Hay-Kaufman et al. . |
| 4,873,187 | 10/1989 | Taub . |
| 4,931,385 | 6/1990 | Block et al. . |
| 4,965,187 | 10/1990 | Tonelli . |
| 5,006,464 | 4/1991 | Chu et al. . |
| 5,028,535 | 7/1991 | Buechler et al. . |
| 5,032,503 | 7/1991 | Khanna et al. . |
| 5,047,326 | 9/1991 | Pronovost . |
| 5,075,220 | 12/1991 | Pronovost . |
| 5,079,171 | 1/1992 | Senyei et al. . |
| 5,081,010 | 1/1992 | Cummins et al. . |
| 5,089,391 | 2/1992 | Buechler et al. . |
| 5,096,830 | 3/1992 | Senyei et al. . |
| 5,132,205 | 7/1992 | Pronovost et al. . |
| 5,136,027 | 8/1992 | Pope . |
| 5,156,948 | 10/1992 | Christensen et al. . |
| 5,185,127 | 2/1993 | Vonk . |
| 5,212,061 | 5/1993 | Snyder et al. . |
| 5,296,192 | 3/1994 | Carroll et al. . |
| 5,384,264 | 1/1995 | Chen et al. . |
| 5,391,478 | 2/1995 | Greene et al. . |
| 5,393,658 | 2/1995 | Olsen . |
| 5,424,193 | 6/1995 | Pronovost et al. . |
| 5,451,347 | * 9/1995 | Akhavan-Tafti et al. ........... 252/700 |
| 5,500,375 | 3/1996 | Lee-Own et al. . |
| 5,571,667 | * 11/1996 | Chu et al. ................................ 435/5 |

OTHER PUBLICATIONS

Bird, R. Byron, Transport Phenomena, Chapter 17 pp. 526–529. Copyright 1960 John Wiley & Sons, Inc.*

* cited by examiner

Primary Examiner—Christopher L. Chin
Assistant Examiner—Pensee T. Do
(74) Attorney, Agent, or Firm—Flehr Hohbach Test Albritton & Herbert LLP; David J. Brezner

(57) ABSTRACT

An analytical device comprising a surfactant-treated porous reaction membrane having an exposed sample-contacting surface and at least one receptor area located in a limited region of the exposed sample-contacting surface. The limited region has a higher concentration of surfactant than areas of the sample-contacting surface that are peripheral to the limited region. To make the device, a surfactant-containing solution comprising at least 0.2% surfactant is added to the reaction membrane and allowed to dry. Then, a receptor reagent is added to a limited region of the reaction membrane. In the assay, the surfactant causes the liquid sample to flow faster through the portion(s) of the reaction membrane where receptor molecules are located.

19 Claims, 6 Drawing Sheets

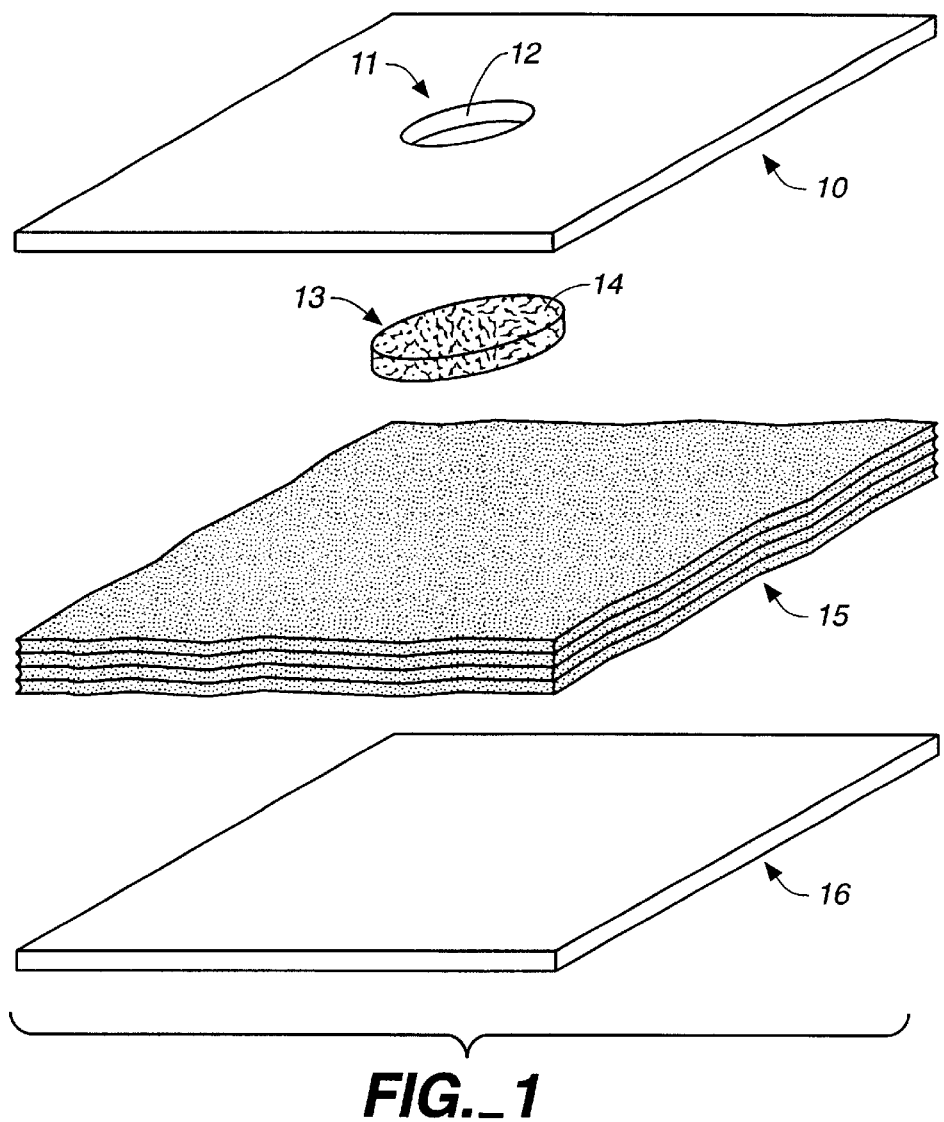
FIG._1
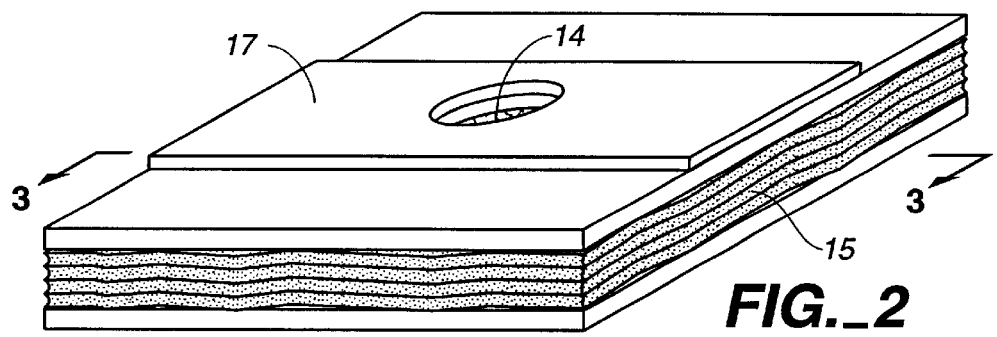
FIG._2

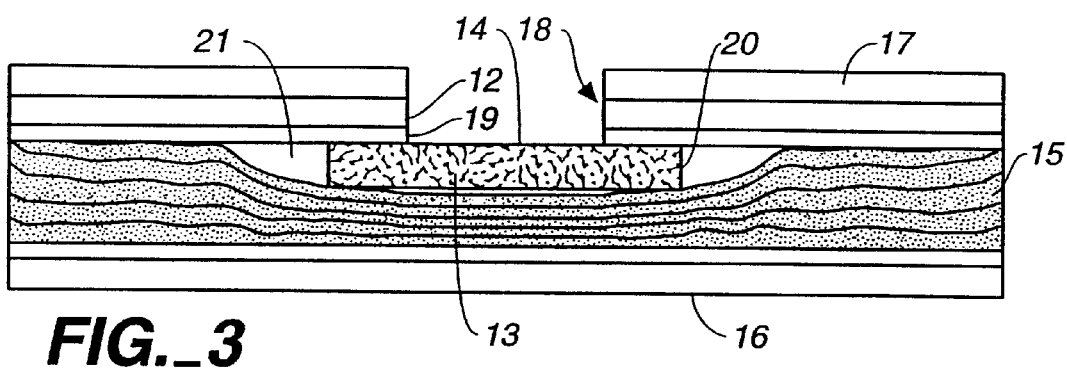
FIG._3

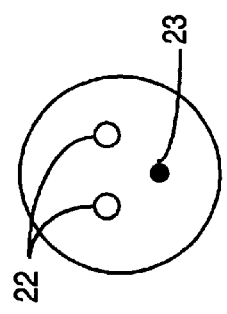
FIG._4C
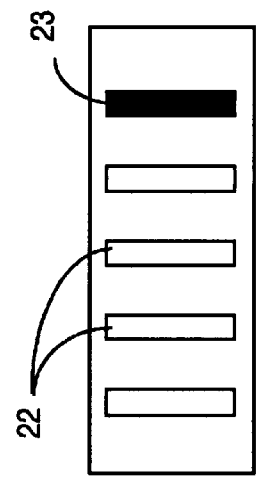
FIG._4F
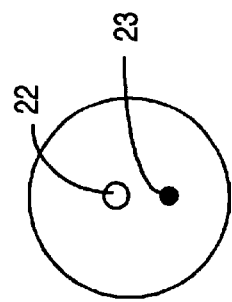
FIG._4B
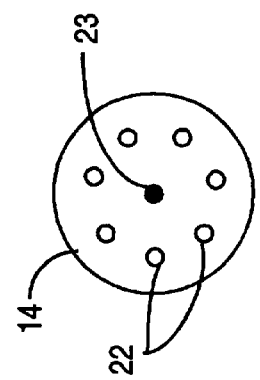
FIG._4E
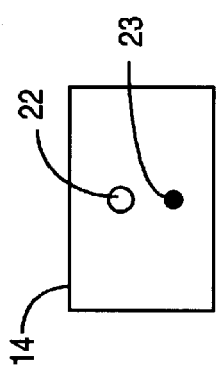
FIG._4A
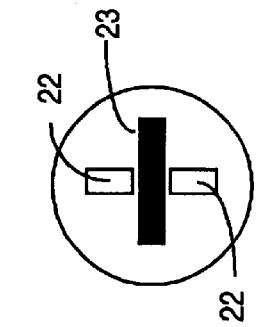
FIG._4D

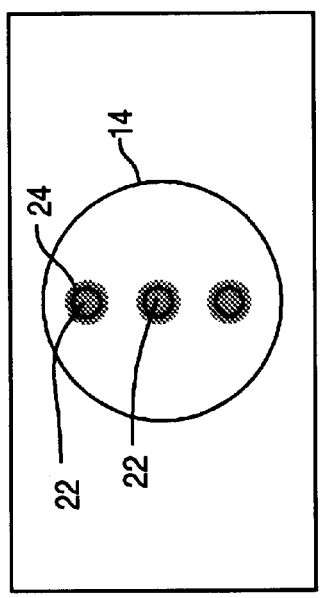
FIG._6
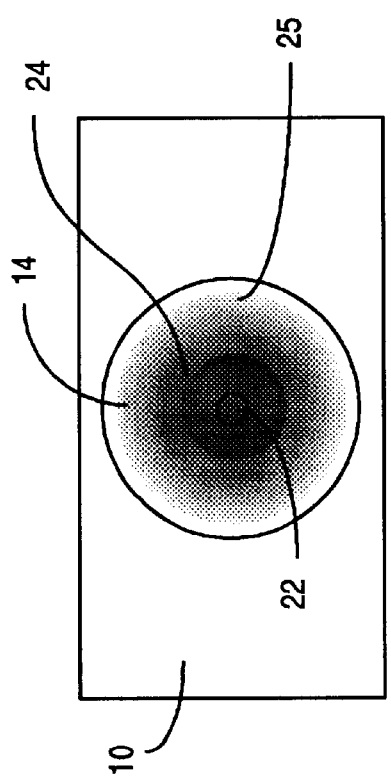
FIG._5

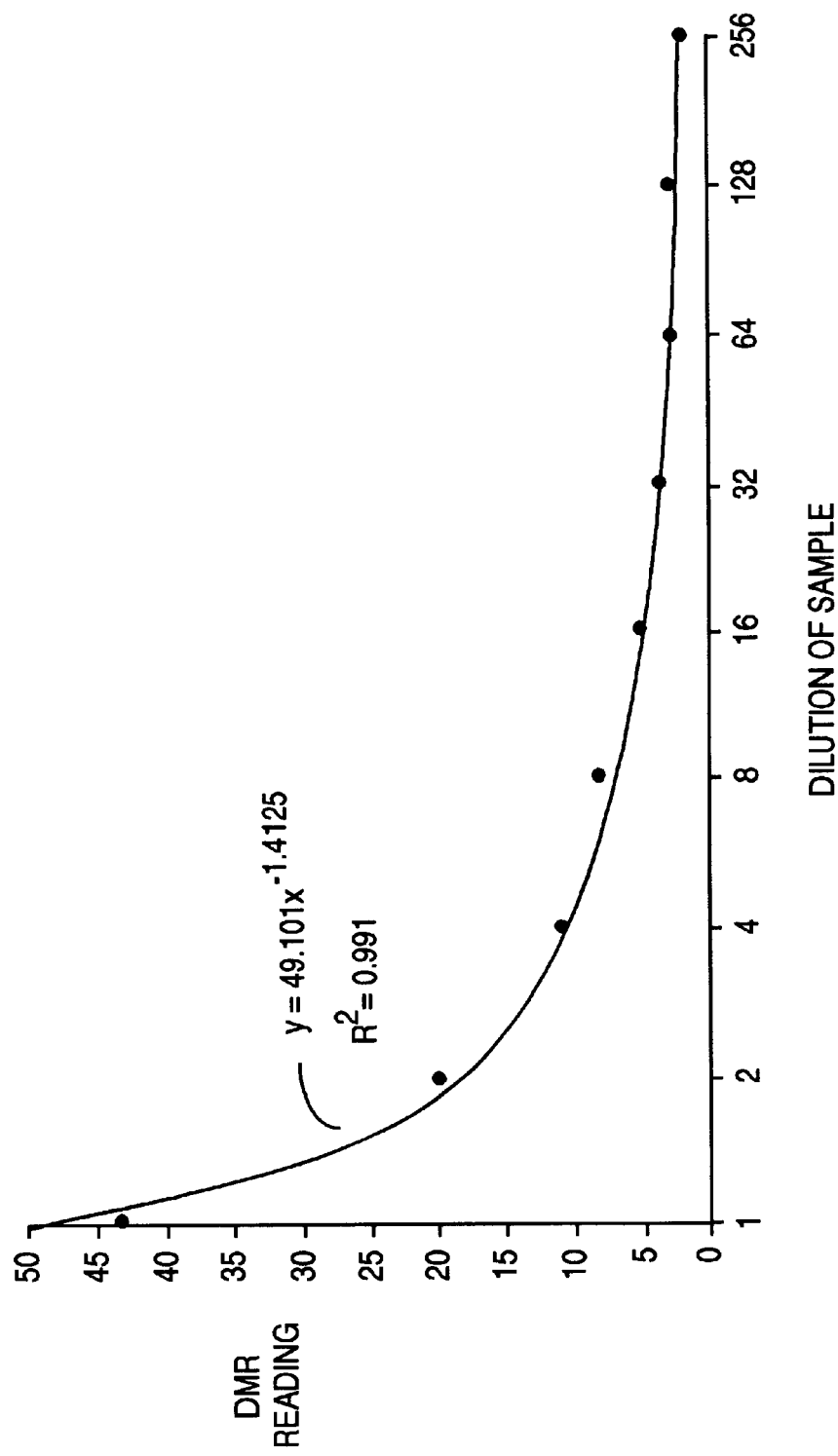
FIG._7

ANALYTICAL ASSAY DEVICE AND METHODS USING SURFACTANT TREATED MEMBRANES TO INCREASE ASSAY SENSITIVITY

BACKGROUND OF THE INVENTION

The technical field of this invention concerns analytical devices and methods for determining the presence of a bindable target substance (i.e. analyte) in a liquid sample possibly containing such substance. Various types of analytical devices, and methods employing the devices, have been used for this purpose. Many of these devices employ reaction membranes onto which a receptor capable of specifically binding to the target substance, is immobilized. In the assay that employs these types of devices, typically the sample to be tested is applied to the reaction membrane. If target substance is present in the sample, it binds to the immobilized receptor. Various methods are used to determine whether the target substance has bound to the receptor, thus indicating its presence in the sample. For immunoassays, where the target substance is an antigen, it is common to use antibodies that are capable of specifically binding to the antigen and that are labeled with detectable markers. When the labeled antibody is added to the reaction membrane, it will bind to the target antigen, if present, and the marker (e.g. fluorescent label, colored reagent, detectable enzyme marker, etc.) is detected.

Membrane-based analytical assays and devices have greatly simplified medical diagnostics. The results of a membrane-based analytical assay can be obtained in a matter of minutes. Quantitative results can be provided by special instruments designed to read the test results. Various types of membrane-based analytical assays are described in U.S. Pat. No. 5,006,464 to Chu et al., U.S. Pat. No. 4,818,677 to Hay-Kaufman et al., and U.S. Pat. No. 4,632,901 to Valkirs et. al., and U.S. Pat. No. 5,185,127 to Vonk et al. There is a continued need to further simplify membrane-based analytical assays and to provide more rapid and more sensitive assays.

SUMMARY OF THE INVENTION

The invention is directed to analytical devices, methods of assembling the analytical devices and assays employing the analytical device for use in the detection of a target substance in a liquid sample. The analytical device comprises a surfactant-treated porous reaction membrane having an exposed sample-contacting surface and at least one receptor area located in a limited region of the exposed sample-contacting surface. The limited region has a higher concentration of surfactant than areas of the sample-contacting surface that are peripheral to the limited region. The analytical device is prepared by assembling an analytical device comprising a porous reaction membrane having an exposed sample-contacting surface, applying a surfactant-containing solution comprising at least 0.2% surfactant to the reaction membrane and allowing it to dry, and applying a receptor reagent to a limited region of the reaction membrane before, after, or at the same time as the surfactant-containing solution is applied to the reaction membrane. In performance of the assay, the surfactant causes the liquid sample to flow faster through the portion(s) of the reaction membrane where receptor molecules are located, relative to areas of the reaction membrane where receptor molecules are not located, thereby increasing assay sensitivity. In one embodiment of the invention, the surfactant is applied to the same limited region of the reaction membrane where receptor molecule is, or will be applied.

BRIEF DESCRIPTION OF THE DRAWINGS

FIG. 1 is an exploded view of an analytical assay device that can be used in the practice of the invention.

FIG. 2 is a top view of an assembled analytical assay device that can be used in the practice of the invention.

FIG. 3 is a cross-section elevation view of the layers of the analytical device of FIG. 2 along the plane 3—3.

FIGS. 4a to 4f show that the configuration of the receptor area(s) and the shape of the reaction membrane can vary.

FIG. 5 is a top view of an analytical assay device, and depicts a surfactant-treated reaction membrane having a higher concentration of surfactant at its central region compared to its peripheral region.

FIG. 6 is a top view of an analytical assay device with a reaction membrane that has receptor areas located where there is a higher concentration of surfactant.

FIG. 7 shows a dosage response curve obtained using the analytical assay device for the detection of antibody to cytomegalovirus in a serum sample.

DETAILED DESCRIPTION OF THE INVENTION

Figure 8:
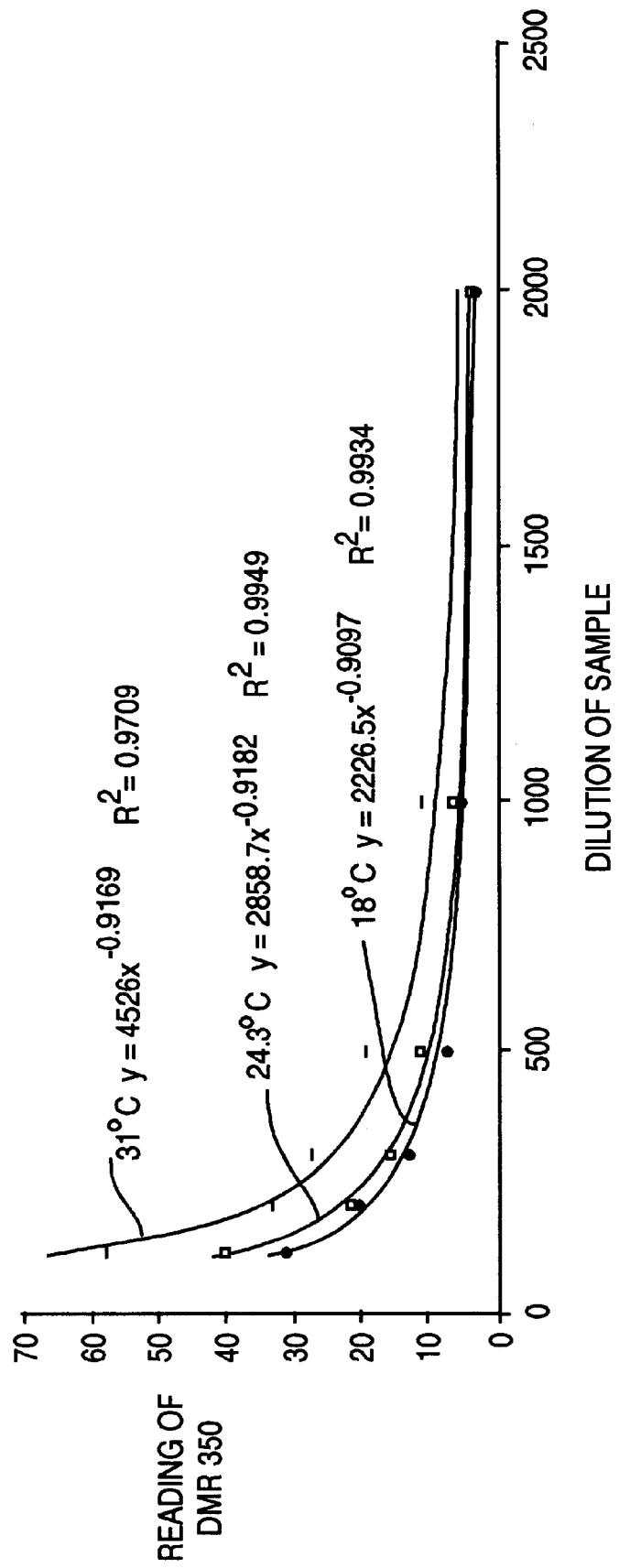
FIG. 8 shows the effect temperature can have on endpoint sensitivity of an immunoassay using the analytical assay device of the invention.

The invention is directed to analytical assay devices and methods that can be used for the rapid detection of a bindable target substance in a liquid sample potentially containing the target substance. The devices employ reaction membranes onto which a receptor capable of specifically binding to the target substance, is immobilized. More particularly, the invention is directed to analytical assay devices comprising membranes that have been treated with a high concentration of surfactant that increases sample flow through the receptor area of the reaction membrane and improves assay sensitivity. References herein to "a surfactant" can refer to surfactant mixtures as well as single surfactants. The analytical devices are relatively easy to manufacture and inexpensive, and the assays utilizing the analytical devices can be performed easily and rapidly. The devices are suitable for use in a variety of assays where a receptor specifically binds to a target substance. The device can be used to test for the presence of target substances in patient samples, for example human serum or blood, or in non-patient samples, such as water. Possible target substances in patient samples include, but are not limited to, specific classes of antibodies such as IgA or IgM; antibodies to specific antigens such as cytomegalovirus (CMV) human immunodeficiency virus I & II (HIV I & II), Epstein-Barr virus (EBV), and H. pyelori; cardio-markers such as myoglobin, troponin I, and fatty acid binding protein; and serum proteins such as alpha fetoprotein. A more complete list of possible target substances is provided in U.S. Pat. No. 5,571,667. Possible types of assays that the devices can be used in include, but are not limited to, antibody/antigen immunoassays, nucleic acid hybridization assays, lectin-carbohydrate assays, avidin-biotin assays, and the like.

Various configurations of an analytical assay device can be used in the practice of the invention. Suitable devices are already known in the art and are disclosed in U.S. Pat. No. 5,006,464 to Chu et al., U.S. Pat. No. 4,818,677 to Hay-Kaufman et al., and U.S. Pat. No. 4,632,901 to Valkirs et al. The device disclosed in co-pending application Ser. No. 08/823,936, is a preferred device for use in the practice of the invention because it is relatively inexpensive and easy to manufacture in comparison with other analytical assay devices. Briefly, referring to FIGS. 1 to 3, the analytical device typically comprises a housing unit or top and bottom support members (10 & 16) which hold together and contain a reaction membrane (13) in fluid communication with an absorbent body (15). The top of the housing or top support member (10) has an open area or port (11) which exposes a portion of the upper surface (14) of the reaction membrane (13). During the performance of the assay, the liquid sample to be tested for the presence of a target substance is applied to the exposed surface of the reaction membrane. A limited region of the upper surface of the reaction membrane has a receptor adhered thereon to which the target substance, if present in the liquid sample, specifically binds. This limited region is referred to herein as the "receptor area" (22). The upper surface of the reaction membrane may optionally have a "control area" (23), which contains a control substance that, upon completion of the assay, indicates whether or not the assay was properly performed. Various types of control substances are known in the art. For example, the use of Protein A control regions are disclosed in U.S. Pat. No. 5,541,059. As known in the art, and as discussed in more detail in copending application Ser. No. 08/823,436, more than one type of receptor molecule can be immobilized onto the reaction membrane at multiple receptor areas to test for the presence of multiple target substances (i.e. analytes) in the sample. This is indicated in FIGS. 4c, 4e, and 4f, which show multiple receptor areas (22).

Any suitable porous material capable of immobilizing the receptor reagent employed in the analytical assay, can be used for the reaction membrane. Suitable materials include nitrocellulose, glass fiber, polyester, cellulose nitrate, polyester, polycarbon, nylon and other natural and synthetic materials which can be coupled directly or indirectly to the selected receptor. Generally, the reaction membrane is hydrophobic and comprises positive and/or negative charges that allow the receptor molecule to bind. Certain membrane materials are charged, such as cellulose nitrate which has partial negative charges contributed by the nitro groups. Other materials may be pre-treated to provide a charged membrane. For example, polyester can be derivatized with carboxyl or amino groups to provide either a negatively or positively charged membrane. Nylon can be treated with acid to break peptide bonds to provide positive charges (from the amine groups) and negative charges (from the carboxyl groups). Porosity of the reaction membrane can also have a significant influence on the flow rate of the sample and assay sensitivity. For most assays, the porosity of the membrane is preferably in the range of about 0.1 to about 12 microns, and more preferably about 0.45 to 3 microns. U.S. Application Ser. No. 08/823,936, discloses additional membrane properties that may influence assay results.

The term "reaction membrane" is intended to include the porous material to which the liquid sample is applied during the performance of the analytical assay, as well as additional porous supporting material, if any, that forms the lower surface of the reaction membrane. For example, a preferred reaction membrane comprises a sheet of nitrocellulose backed with a porous paper. Commercially available porous polyester supported nitrocellulose can also be used. A representative example of paper-backed nitrocellulose is commercially available from EY Laboratories Inc. (San Mateo, Calif.; Cat. Nos. PBNC15-1, PBNC15-10, PBNC15M-1, and PBNC15M-10). This preferred membrane is substantially more durable than nitrocellulose alone and can be employed without any other support component. This allows for easier handling and device assembly. It has been found that older lots of nitrocellulose are more hydrophobic than new lots, and provide increased assay when surfactant treated according the methods described herein. This is presumably because when sample is added to the reaction membrane, it tends to flow more readily through the portions of the reaction membrane that have a high surfactant concentration as opposed to the more hydrophobic portions of the membrane. It will appreciate that the properties of a reaction membrane of a specified material can vary from lot to lot, and with age. Therefore, quality control testing, using standard controls, is performed in order to determine the suitability of a particular membrane for a given analytical assay.

Unlike typical membrane-based analytical devices, the analytical devices of the present invention are preferably assembled using reaction membranes that have not been blocked with protein-containing reagents. The term "blocked" is understood by those skilled in the art of membrane-based analytical assay design to refer to the treatment of a reaction membrane with a composition that prevents the non-specific binding of the target substance to the reaction membrane. Typically a blocking composition comprises a protein, such as casein or albumin, and may additionally comprise surfactants. The function of the protein is to bind to the reaction membrane to prevent the sample and/or assay reagents from binding non-specifically to the reaction membrane. Because the analytical assay devices of the present invention preferably do not employ blocked reaction membranes, and blocking steps are not required during the performance of the assay, the devices are more simple to manufacture than typical analytical assay devices, and the assays are easier to perform.

After the analytical devices are assembled, for example, using the methods detailed in co-pending application Ser. No. 08/823,436, the reaction membrane is treated with a solution that contains a high concentration of surfactant. The phrase "treated with a surfactant", means simply that a surfactant-containing solution has been applied to all or part of the exposed surface of the reaction membrane, and allowed to sufficiently dry prior to performing an analytical assay. Best results are usually achieved when the surfactant containing solution consists essentially of the surfactant and the solvent used to prepare the solution (e.g. water, alcohol, or other solvent). However, in some applications, it may be desirable to have other additional components included in the surfactant-containing solution. As discussed in more detail below, one or more receptor areas is also formed on the reaction membrane in a manner such that the resulting reaction membrane contains a higher concentration of surfactant at portions of the exposed surface of the reaction membrane where receptor areas are located relative to portions of the exposed surface of the reaction membrane that are peripheral to the receptor areas.

The inventor discovered that when the reaction membrane is treated with certain surfactant-containing solutions having high concentrations of surfactant, greater than about 0.2 percent, and usually in the range of about 0.2 to about 15.0 percent (although higher concentrations can sometimes be used depending upon the solubility of the surfactant), increased flow of the sample and other reagents through the center of the reaction membrane where the receptor molecule is typically located, can be achieved. In typical membrane-based analytical assays, increased sample flow equates to a shorter reaction time between the target substance in the liquid sample and the receptor molecule located on the reaction membrane, and results in decreased assay sensitivity. However, with the analytical devices of the present invention, there is increased sample flow where the receptor area(s) is located, and reduced sample flow at portions of the membrane where there are no receptor areas, causing more sample to flow through the receptor area. Thus, the higher concentration of surfactant at the receptor area in effect, acts as a funnel that directs sample flow to the region of the membrane where receptor is located. This has the net effect of increasing assay sensitivity. The increase in assay is surprising because surfactants are commonly used in membrane-based analytical assays to wash non-specific binding from the membrane, which usually results in washing away some specific binding as well, and thus reduces sensitivity. However, it is believed that the surfactant treatment described herein, actually facilitates binding between the receptor molecule and target substance. As used herein, all references to the concentration of surfactant in the surfactant-containing solutions used to treat the reaction membrane, or in the wash buffers described below, are expressed in terms of percentage by volume, where the surfactant used to make the solution is in liquid form, or percentage by weight, where the surfactant used is in the form of a solid. For example, a composition prepared by mixing 5 ml. of TRITON® X-45 in 95 ml. water, contains 5% surfactant. A solution prepared by dissolving 5 grams of sodium cholate in water to achieve a final volume of 100 ml.

In one embodiment of the invention, the surfactant treatment is done by applying a surfactant-containing solution to the exposed surface of the reaction membrane of an already-assembled analytical device, in an amount sufficient so that all, or most of the exposed surface is contacted with the surfactant. Depending upon the surfactant used, the concentration of surfactant is typically in the range of about 0.2 to about 15.0%, and more typically in the range of about 0.2 to about 5.0%. Usually, a concentration of approximately 0.5 to about 2.0%, is preferred, with about 1.0% being most preferred. The surfactant can be diluted in water, alcohols, or other suitable solvents (many commercial surfactants comprise proprietary solvent bases). Typically, about 20 to 50 µl surfactant-containing solution is used to treat a reaction membrane having an exposed surface area of 1 cm². More or less surfactant is used depending upon the surface area to be treated. The surfactant flows through the reaction membrane and into an absorbent layer below. Without being limited to any particular theory of mechanism of action, it is believed that as the surfactant dries, there is a venting action of the already-assembled analytical assay device that causes a back-flow of the surfactant from the absorbent layer back into the central region of the reaction membrane. This in turn, is believed to result in a higher concentration of surfactant at the central portion of the exposed surface of the reaction membrane compared to the periphery of the exposed surface of the reaction membrane. It is believed that this surfactant pre-treatment results in a reaction membrane that has a concentration of surfactant at its center that is at least two times more concentrated than the concentration of surfactant at areas peripheral to the central portion of the exposed surface of the reaction membrane.

The "central portion of the exposed surface of the reaction membrane", is depicted in FIG. 5 as a darkened region (24). The term "central portion" refers to the portions of the reaction membrane that are closer to the center of the exposed surface of the reaction membrane than the edge of the exposed surface of the reaction membrane. The periphery of the exposed surface of the reaction membrane is depicted as the more lightly shaded region (25), and has approximately the same as, or more total surface area than the central portion. During performance of the assay, the higher concentration of surfactant at the central portion of the exposed surfaces of the reaction membrane, relative to the periphery of the reaction membrane, acts like a funnel, causing the liquid sample to more readily flow through the center of the reaction membrane where the receptor area (22) is typically located, thereby providing increased assay sensitivity. With this embodiment of the invention, more than one receptor molecule can be used to form multiple receptor areas. If this is done, the receptor areas are typically limited to the central region of the exposed surface of the reaction membrane where there is a higher concentration of surfactant.

Preferred surfactants that achieve the above-described back-flow/funnel effect are anionic surfactants having molecular weights of less than about 1,000. More preferably, the anionic surfactant used in the surfactant-containing solution has a molecular weight of less than about 800, and even more preferably, less than about 500. The surfactant-containing solution usually comprises at least 0.2% surfactant. Some anionic surfactants, such as sodium dodecyl sulfate (SDS), will work at lower concentrations. However, as the sensitivity achieved with SDS is generally low, it is not a preferred surfactant for some assays. A preferred surfactant-containing solution comprises from about 0.2% to about 2% of a cholic acid surfactant. When less than about 0.1% cholic acid surfactant is used to treat the membrane, sample flow decreases and sensitivity is reduced. This is presumably due to an insufficient differential between the concentration of surfactant at the central portion of the reaction membrane, and the concentration of surfactant at the periphery of the reaction membrane, thereby lessening funnel effect previously described. As used herein, the term "a cholic acid" or "cholic acids" refers to cholic acid, derivatives of cholic acid such as deoxycholic acid, taurocholic acid, taurodeoxycholic acid, taurochenodeoxycholic acid, and salts thereof. As will be described in more detail, the increased assay sensitivity is achieved when used in conjunction with detection reagents, such as Protein A/colloidal gold, that have been prepared in suitable detergents.

In another embodiment of the invention, only the portion of the reaction membrane where receptor reagent(s) is (or will be) located, is treated with the surfactant-containing solution. With this embodiment of the invention, a higher concentration of surfactant is generally used compared to when the entire exposed surface of the reaction membrane is treated. Usually, concentrations of surfactants in the range of about 0.5% to about 15.0% are used, preferably about 2.5% to about 15.0%, and more preferably about 4.0% to about 12.0%. With some surfactants, higher concentrations may be used, depending upon their solubility in water. With this embodiment of the invention, the volume of surfactant-containing solution added to the reaction membrane will usually be about the same as the volume of receptor reagent added to form the receptor area. For example, if it is desired that the receptor area have a diameter of approximately 2 to 5 mm, then about 0.5 to about 2.5 µl of surfactant-containing solution is spotted onto the receptor area. Although, the amount of surfactant-containing solution can differ somewhat from the amount of receptor reagent that is added.

An advantage of confining application of the surfactant-containing solution to the limited regions where the receptor areas are, or will be located, is that the funneling effect that is achieved by the surfactant treatment can be located any place on the exposed surface of the reaction membrane where it is desired. This is particularly advantageous if multiple analytes are to be tested, requiring the use of multiple receptors on different locations of the reaction membrane. With this embodiment of the invention, limited region (or regions) of the exposed surface of the reaction membrane will contain both surfactant and receptor reagent, whereas portions of the reaction membrane that are peripheral to the limited region (or regions), will not contain receptor reagent or surfactant. This is depicted in FIG. 6, in which is shown a reaction membrane having 3 receptor areas (22) located within 3 limited regions of the reaction membrane that have been treated with a high concentration of surfactant (24). The receptor molecule used at each receptor area can be different, such that multiple analytes can be tested at the same time. With this embodiment of the invention, the reaction membrane can be treated with the surfactant-containing solution before the analytical device is assembled because the previously described back-flow action is not needed to achieve the desired funnel effect. However, it is usually preferable to do the surfactant treatment after assembly of the analytical device because it is easier to keep track of the areas of the reaction membrane that have been treated with the surfactant.

The surfactants that provide the best results in this embodiment of the invention do not have any apparent unifying structural or charge characteristics. Anionic, cationic, zwitterionic, non-ionic have all been found to work. Additionally, while lower molecular weight surfactants have been found to work best in the embodiment of the invention where back-flow of surfactant to the center of the reaction membrane is relied upon to achieve the increased concentration of surfactant at the central portion of the reaction membrane, both high and low molecular weight surfactants work well in the embodiment of the invention where the surfactant-containing solution is applied to a limited region of the reaction membrane. One common feature of most of the surfactants that work is that, in order to prepare a 10% solution of these surfactants in water, alcohol, or other solvent at room temperature, relatively long periods of vigorous stirring (usually at least 10 minutes, sometimes 6 to 12 hours or more) are generally required. Heat can be used to facilitate getting the surfactant into solution, but care must be taken that the surfactant remains in solution and does not form a precipitate.

Anionic surfactants that can be used in the practice of the invention include, but are not limited to, cholic acid surfactants (e.g. cholic acid, deoxycholic acid, taurocholic acid, taurodeoxycholic acid, and their salts), sodium dioctylsulfosuccinate, sodium N-oleyl-N-methyltaurate (available under the trade name GEROPON® T-77, lithium dodecyl sulfate, sodium dodecyl sulfate, sodium olefin (C14–C16) sulfonate (such as Bioterge® AS40 from Stepan Chemical), sodium polyoxyethylene lauryl sulfates (such as Standapol® ES-1 available from Henkel Corp.); poly(methylvinylether-co-maleic) anhydride (GANTREZ AN-119); sodium carboxymethylcellulose (CELLULOSE GUM 7LF); sodium polystyrenesulfonate (FLEXAN 130); sodium carageenin (VISCARIN GP309); and acrylic latex (UCAR 456). A cationic surfactant that can be used in the invention includes, but is not limited to, benzalkonium ($C_8$–$C_{18}$) chloride. Zwitterionic surfactants that can be used in the invention include, but are not limited to, CHAPS (3-[(3-cholamidopropyl)dimethylammonio]-1-propanesulfonate); CHAPSO (3-[(3-cholamidopropyl)dimethylammonio]-2-hydroxy-1-propane-sulfonate); N-dodecyl-N,N-dimethyl-3-ammonio-1-propane- sulfonate (Sulfobetaine® SP 12); N-tetradecyl-N,N-dimethyl-3-ammonio-1-propane sulfonate (Sulfobetaine® SP 14); ethylenediamine alkoxylate block copolymer (Tetronic® 1307); and bony fish gelatin (TELEOSTEAN gelatin). Non-ionic surfactants that can be used in the practice of the invention include, but are not limited to, polyoxyethylene (23) dodecyl ether (BRIJ® 35); isotridecylpoly (ethyleneglycol ether)$_n$ (GENAPOL® X-080); ethylphenolpoly(ethyleneglycolether)$_n$ (Nonidet® P-40); polyethyleneglycol-polypropylene glycol copolymer (Synperonic® PE/F68, and PE/F127); dodecylpoly (ethyleneglycolether)$_n$ (Thesit®); 2,4,7,9-tetramethyl-5-decyne-4,7-diol ethoxylate(10) (Surfynol® 465); 2,4,7,9-tetramethyl-5-decyne-4,7-diol ethoxylate(30) (Surfynol® 485); octylphenol ethoxylate(1.2) (IGEPAL® CA210); octylphenoxypolyethoxy(5) ethanol (TRITON® X-45); octylphenoxypolyethoxy(9-10) ethanol (TRITON® X-100); octylphenoxypolyethoxy(10-11) ethanol (TRITON® X-114); octylphenoxypolyethoxy(30) ethanol (TRITON® X-305); polyoxyethylene(20) sorbitan monolaurate (Tween® 20); polyoxyethylene(20) sorbitan mono-oleate (Tween® 20); polydimethylsiloxane methylethoxylate (SILWET® L7600); polyethoxylated oleyl alcohol (RHODASURF® ON-870); polyethoxylated (35) castor oil (Cremophor® EL); polyoxyethylene(9) lauryl alcohol (CHEMAL® LA-9); poly(oxyethylene-co-oxypropylene) block copolymer (Pluronic® L64); polyethylene glycol (mol. wt. 8,000); p-isononylphenoxypoly(glycidol) (SURFACTANT 10G); Sorbitan monostearate (SPAN® 60); polyvinylpyrrolidone (PVP K-30; PVP K-90); polyethylene oxide (POLYOX WSR-301 ); polyvinylalcohol (ELVANOL 71-50); hydroxypropylcellulose (KLUCEL EEF); hydroxyethylcellulose (NATROSOL 250LR).

Preferred surfactants for use in the practice of the invention include polyethylene glycols (preferably having molecular weights less than about 8,000), amine alkyl benzene sulfonates (such as NINATE® 411 available from Stepan Chemical), sodium N-oleyl-N-methyltaurate, sodium olefin (C14–C-16) sulfonate (such as Bioterge® AS40 from Stepan Chemical), ammonium lauryl sulfates, (such as Standapol® ES-1 available from Henkel Corp.), octyl phenoxy polyethoxy ethanols (e.g. TRITON® X-45, available from Rohm & Haas), dimethicone copolyols (such as Silwet® L7600 from Union Carbide), polyethoxylated oleyl alcohols (such as Rhodasurf ON-8700), and cholic acid surfactants. As already noted, cholic acid surfactants, and other low molecular weight anionic surfactants, work particularly well in the embodiment of the invention wherein the entire exposed surface of the reaction membrane is treated with the surfactant, and the action of back-flow is relied upon to achieve a higher concentration of surfactant at the central portion of the exposed surface of the reaction membrane.

Different surfactants will work best for different assays, and in some cases, combinations of certain surfactants may work best. When combinations of surfactants are used, the total concentration of surfactant in the surfactant-containing solution will be generally in the range of 0.2 to about 15.0 percent. Generally, as the concentration of surfactant increases, sample flow rate increases. In the case of an immunoassay for the detection of antibody to HIV, it has been found that a surfactant-containing solution comprising about 3.3% sodium cholate, 3.3% sodium deoxycholate, and 3.3% Bioterge AS40 (a sodium salt of C14–C16 olefin sulfonates; from Stepan Chemical), applied to the portion of the reaction membrane where the receptor area is located, gives good results after suitable drying.

The list of suitable surfactants provided herein is not intended to be limiting. One skilled in the art, provided with this disclosure, can readily determine, using routine experimentation, other surfactants that provide suitable results. For example, a candidate surfactant or combination of surfactants could be readily tested for its suitability in a particular assay by preparing various dilutions of the surfactant(s), applying the various dilutions to the reaction membranes of already-assembled assay devices in the manner described above, allowing the reaction membranes to dry, applying the receptor reagent (before, after, or the same time as surfactant treatment), and performing the desired analytical assay.

The surfactant-containing solution is usually added before or after application of the receptor-containing composition to the reaction membrane. However, for some assays adequate results can be achieved when the receptor molecule and the surfactant-containing are pre-mixed and added to the reaction membrane at the same time. When the entire reaction membrane is treated with the surfactant, and the above-described back-flow action is relied upon to provide an increased concentration of surfactant at the central portion of the exposed surface of the reaction membrane, then application of the receptor reagent is done in a separate step before or after surfactant treatment. With some assays, higher sensitivity is achieved when the receptor-containing composition is added to the reaction membrane prior to surfactant treatment. With other assays, better results are achieved when the surfactant treatment is first. Whether the order of addition will have an effect on assay results can be readily determined using routine experimentation. Best results are usually achieved when the reaction membrane is allowed to sufficiently dry between the addition of the surfactant-containing solution and the receptor-containing composition. Typically, at least four hours of room temperature drying is required at relatively low humidity. If humidity in the environment is high, then drying times will probably be longer. If the surfactant-containing solution is applied to the entire surface of the reaction membrane, then usually about twelve hours of room temperature drying is required. The required time for the drying process can be reduced using warm air, a low humidity environment, and good ventilation. However, care must be taken that the humidity is not too low, and the heat too high, or the reaction membrane can become brittle and crack.

The receptor-containing composition typically comprises the receptor molecule diluted in a suitable buffer or water. The receptor molecule can be any molecule capable of specifically binding to a target molecule in a sample and capable of being bound to the reaction membrane. Various types of receptor molecules include antigens, antibodies, nucleic acid, lectin, carbohydrates, and the like. If the receptor molecule is an antigen, the diluent may be selected to solubilize the antigen to provide maximum epitope exposure to increase assay sensitivity. Generally, buffers such as Tris buffer and phosphate buffered saline (PBS), having a pH in the range of about 6.5 to 8.5, are suitable diluents. Oftentimes, an antigen that is obtained commercially, such as HIV, is prepared in a surfactant diluent, such as SDS. In this case, best results may be obtained if the antigen is diluted in water to prepare the receptor-containing composition. One skilled in the art of immunodiagnostics will appreciate that routine experimentation can be used to determine a suitable diluent for a particular receptor molecule.

Typically, the receptor-containing composition is spotted, dropped, printed, or biojected onto the reaction membrane, using methods known in the art, so that the receptor molecule is adhered to a limited portion of reaction membrane.

In the simplest embodiment of the invention, a drop of receptor-containing composition is spotted onto the center of the reaction membrane so that a circular receptor area forms, as depicted in FIGS. 4a to 4c. For a circular receptor area having a diameter of approximately 2 to 4 mm on a nitrocellulose reaction membrane, approximately 0.5 to 2.5 $\mu$l of the receptor-containing composition is added to the center of the reaction membrane. Other methods can be used to achieve receptor areas having different shapes. For example, bar-shaped receptor areas, as depicted in FIG. 4d, can be used to form plus and minus signs as described in U.S. Pat. No. 4,916,056.

In use, a biological sample to be tested for the presence of a target substance is added to the exposed surface of the reaction membrane. It has been found that the results of immunoassays employing the analytical devices described herein can be temperature dependent, as discussed in Example 6 below, and depicted in FIG. 8. Therefore, in assays where endpoint sensitivity is important, it may be preferred to perform the assays in a heated room or pre-warm the sample and other reagents before use. In the embodiment of the invention where only a limited region of the exposed surface of the reaction membrane is treated with the surfactant-containing solution, it may be desirable, before beginning the assay, to pre-wet the reaction membrane with a detergent-containing solution or buffer (e.g. Tris), to increase flow rate of sample and decrease non-specific binding. However, this can sometimes decrease assay sensitivity. Therefore, membrane pre-wetting is generally not done when it is important to achieve the most sensitive assay results. Depending on the target substance and the type of sample (e.g. blood, serum, saliva, etc.), the sample may be pretreated, for example by filtering or detergent extraction, using methods known in the art to improve assay results.

After the sample is added to the reaction membrane, an appropriate detection reagent is added which specifically binds to the target substance, if present at the receptor area. The term "specifically binds" means that there is either a direct binding between the target substance and the detection reagent, or an indirect binding, where an intermediate reagent specifically binds to the target substance, and the detection reagent specifically binds to the intermediate reagent to indicate the presence of the target substance. Prior to addition of the detection reagent, a wash buffer may be added to remove residual sample from the reaction membrane. However, in a preferred embodiment of the invention, the detection reagent is formulated in a detergent base that washes away residual sample. Thus, the wash and detection steps are combined into one, which simplifies the assay. A preferred detection reagent is Protein A/colloidal gold diluted in a detergent composition that is described in more detail below. The use of Protein A/colloidal gold as a detection reagent is well-known in the art and is discussed in detail in U.S. Pat. No. 5,541,059. Colloidal gold is a preferred label because colloidal gold conjugates are much more simple to prepare and use in comparison with conventional antibody/enzyme conjugates. Colloidal gold is purplish-red in color, and thus can be detected visually without the use of the instrumentation that is required for the detection of other types of markers such as radioactive isotopes, fluorescent markers, and chemiluminescent markers. Furthermore, unlike enzyme markers, colloidal gold particle markers do not require the additional step of adding a substrate.

For use in immunoassays, where the target substance is an antibody, for example, antibody to HIV, a preferred detection reagent is Protein A/colloidal gold diluted in a detergent composition as detailed below. In the case of an HIV immunoassay, the receptor molecule is HIV antigen. If IgG antibody to HIV is present in the sample, it will bind to the receptor reagent. Protein A/colloidal gold then binds to the Fc region of the IgG, and a reddish-purple color is apparent at the receptor area of the reaction membrane. A preferred diluent for the Protein A/colloidal gold is a detergent-containing composition comprising one or more of the following detergents: TRITON® X-305, TRITON® X-100, TWEEN® 20, PLURONIC® L64, and BRIJ® 35. The TRITON® series of detergents are nonionic detergents comprising polyoxyethylene ethers and other surface-active compounds. The PLURONIC® series are nonionic surfactants that are partial esters of block copolymers of poly (oxyethene-co-oxypropylene). The TWEEN® series are derived from the SPAN® products by adding polyoxyethylene chains to the nonesterified hydroxyls. BRIJ® 35 is a trademark of the Pierce Chemical Company, Rockford, Ill., and is a 30% solution of polyoxyethylene lauryl ether detergent. Any combination of the above-listed detergents can be used. Usually, the final concentration of detergent is in the range of from about 0.5% to about 3.0% detergent; about 1.0 to 1.5% detergent usually works best. If much less than 0.5% detergent is used, non-specific binding of sample and reagents may result in background noise that interferes with the assay results. If much more than 3.0% detergent is used, assay sensitivity can be compromised. For an HIV immunoassay, good results have been obtained using a wash buffer having 0.20% of each of the five detergents listed above prepared in a 0.2M Tris buffer. The best combination for a given assay can be determined using routine experimentation. For immunoassays, the final pH of the detection reagent may affect the sensitivity of the assay. Therefore, it will be desirable to determine which buffer provides the best results for a given assay.

In some cases, a purplish-red color at the receptor area, indicating the presence of target substance, will be immediately apparent after addition of the colloidal gold to the reaction membrane, making a final wash step unnecessary if only qualitative results are desired (i.e. test results are either "positive" or "negative". However, if quantitative results are desired, or if the presence of background "noise" (i.e. color on portions of the reaction membrane where the receptor reagent is not present) interferes with the reading of the receptor area, a final wash step can be employed using a water wash, or a detergent composition (which may be the same as or different from the diluent used to prepare the detection reagent). For quantitative results, the receptor area can be measured using any device designed for making such measurements, such as the optical analyzer described in U.S. Pat. No. 5,717,778.

All references, patents, and patent applications cited herein are hereby incorporated by reference in their entireties.

The following examples are for illustrative purposes only and are not to be construed as limiting the scope of the invention in any manner.

EXAMPLE 1

Assembly of Analytical Device

Analytical devices like those described in co-pending application Ser. No. 08/823,936 were prepared using the following components and were assembled as shown in FIGS. 1–3: Top support layers (10) measuring 3.8 cm square were cut from flexible, but rigid polyvinyl chloride (PVC) plastic that had a water-insoluble pressure-sensitive adhesive on one side. Holes 8 mm in diameter were punched into the center of the top support layers. Circular reaction membranes (13), 11 mm in diameter, were punched from paper-backed nitrocellulose having a thickness of approximately 0.8 mm (EY Laboratories Inc. Cat. # PBNC15-1) and adhered to the adhesive side of the top support layer so as to cover the hole. An absorbent body (15) comprised of a 3.8 cm square of absorbent material (from Whatman, Cat. No. F427-05) was adhered to the adhesive side of the top support layer. A bottom support layer (16), measuring 3.8 cm square and comprising the same plastic material and adhesive as the top support layer, was adhered to the lower surface of the absorbent body. A reservoir defining member (17), comprising the same plastic material and adhesive as the top support layer, measuring approximately 3.8 cm×1.5 cm, and having an 8 mm diameter hole punched in the center, was positioned onto the top of the top support layer as shown in FIG. 2.

EXAMPLE 2

Treatment of Reaction Membrane

A. Detergent Treatment of Entire Exposed Surface of Reaction Membrane

A 1% solution of sodium cholate was prepared in water. 40 µl of cholate solution was added to the membrane of a pre-assembled analytical device prepared according to Example 1. The detergent solution completely covered the exposed upper surface of the reaction membrane and was allowed to absorb into the membrane. The membrane was allowed to dry over night at room temperature. After the membrane was completely dried, 0.5 µl of a solution containing 50 ng HIV antigen in 0.5% SDS was spotted onto the center of the reaction membrane and allowed to dry.

B. Detergent Treatment Limited to Receptor Area of Reaction Membrane

A 10.0% solution of sodium cholate was prepared in water. 0.5 µl of the sodium cholate solution was spotted onto the reaction membrane of a pre-assembled analytical device prepared according to Example 1, and allowed to dry for four hours at room temperature. 0.5 µl of a solution containing 50 ng HIV antigen in 0.5% SDS was spotted onto the reaction membrane at the same location where the detergent was spotted, and allowed to dry.

EXAMPLE 3

Preparation of Reagents for Immunoassay

A. Protein A/Colloidal Gold

Lyophilized Protein A/colloidal gold was reconstituted in a wash buffer comprising the following surfactants diluted in 0.2M Tris: TRITON® X-305, TRITON® X-100 TWEEN® 20, PLURONIC® L64, and BRIJ® 35. Each detergent was used in amounts of 0.2% to achieve a final concentration of 1.0% detergent.

EXAMPLE 4

Immunoassay for Detection of HIV Antibody

Normal human serum to which rabbit antibody to HIV 1 was added was serially diluted with normal human serum containing no antibody to HIV. An 80 µl drop of each dilution of human serum was added to the reaction membranes of the devices prepared and treated accordingly to the procedures described in Examples 1 and 2, and allowed to completely absorb. An 80 µl drop of the Protein A/colloidal gold solution described in Example 3 was added to the reaction membrane and allowed to completely absorb. 160 μl of the wash buffer described in Example 3 was added to the reaction membrane to wash unbound reagents through the membrane. At the end of the assay, a purple-red spot was detected on the analytical device prepared accordingly to Example 2A which has a 1/10,000 dilution, indicating that rabbit antibody to HIV 1 was present and detectable at that dilution using the analytical device and the above assay procedures. Using an analytical device prepared according to Example 2B, the 1/100,000 dilution gave a positive result.

EXAMPLE 5

Immunoassay for Detection of CMV Antibody

Analytical assay devices were prepared as described in Example 1. The center of the reaction membrane was inoculated with 0.5 μl CMV antigen (Fritzgerald Ind.) and allowed to dry for four hours. A surfactant-containing solution was prepared containing 3.3% sodium cholate, 3.3% sodium deoxycholate, and 3.3% sodium olefin (C14–C16) sulfonate diluted in water. 0.5 μl of the surfactant-containing solution was spotted onto the receptor area of the reaction membrane (i.e. at the same location where the CMV antigen was spotted).

A Protein A/colloidal gold (EY Labs Lot No. 151231) was diluted in a detergent solution comprising 250 mM Tris, 0.2% TWEEN® 20, 0.2% TRITON® X-350, 0.2% BRIJ® 35, 0.2% CHEMAL® LA-9, and 1.0% TRITON® X-100.

Serial dilutions of a serum sample containing antibody to CMV were made into normal human serum. 40 μl of each dilution were added to the exposed surface of the reaction membrane of the analytical devices. After all of the serum had absorbed into the reaction membrane, 80 μl of the Protein A/colloidal gold-detergent solution were added to the reaction membrane, and allowed to flow through the reaction membrane. Three drops of the detergent solution used to dilute the Protein A/colloidal gold were added to the reaction membrane as a final wash step. Presence of colloidal gold at the receptor area was determined using a Dot Master Reader (DMR), from EY Laboratories, San Mateo, Calif. The DMR reading increases with increasing concentration of colloidal gold at the receptor area. The results are shown in Table I.

TABLE I

| Sample Dilution | 1 | 2 | 4 | 8 | 16 | 32 | 64 | 128 | 256 |
|---|---|---|---|---|---|---|---|---|---|
| DMR reading | 43.4 | 19.9 | 10.8 | 8.1 | 5.3 | 3.7 | 2.9 | 2.7 | 2.0 |

The dosage response curve for this assay is shown in FIG. 7.

EXAMPLE 6

Effect of Temperature on Endpoint Sensitivity of Immunoassay

Analytical assay devices were prepared as described in Example 1. An HIV 1 & 2 antigen conjugate was prepared by conjugating HIV 1 antigen with an HIV II p36 14-mer synthetic peptide using sulfosuccinimidyl 4-(N-Maleimidomethyl)-cyclohexane-1-carboxylate (Sulfo-SMCC, available from Pierce) as a coupling agent (following the procedure described in the Pierce catalog). The resulting HIV 1 +2 antigen was prepared in a final buffer comprising 0.2M phosphate, 0.1 M SDS, and 0.05 M $NaN_3$, at pH 6.5.

0.5 μl of the antigen was spotted onto the center of the reaction membrane of each analytical device. The assay was performed using the procedure described in Example 4, and was carried out at three different room temperatures, 18° C., 24.3° C., and 31° C. Presence of colloidal gold at the receptor area was determined using the same procedure as in Example 5. The results are shown in Table II.

TABLE II

| Temperature Dependence of Assay Sensitivity | | | | | | |
|---|---|---|---|---|---|---|
| Sample Dilution | 100 | 200 | 300 | 500 | 1000 | 2000 |
| DMR reading at 18° C. | 31.11 | 19.91 | 12.58 | 7.38 | 4.54 | 2.07 |
| DMR reading at 24.3° C. | 40.02 | 20.89 | 15.85 | 10.44 | 5.28 | 2.43 |
| DMR reading at 31° C. | 57.7 | 32.96 | 26.81 | 18.58 | 9.22 | 3.36 |

FIG. 8 shows the calibration curves obtained when the above results are plotted. The results show that the end-point of assay sensitivity increased when the assay was performed at a higher temperature.

What is claimed is:

1. An analytical device for use in the detection of a target substance in a liquid sample, said device comprising a porous flow-through reaction membrane having an exposed sample-contacting surface and at least one receptor area located in a limited region of said exposed sample-contacting surface, wherein said reaction membrane contains at least one surfactant having a higher concentration within said limited region relative to the area peripheral to said limited region, and wherein said limited region of said reaction membrane has been pre-treated with a surfactant-containing solution comprising at least about 0.2% surfactant that results in said higher concentration of said surfactant within said limited region, and an absorbent body in fluid communication with the opposite side of said reaction membrane from said sample-contacting surface, whereby liquid sample deposited on said exposed sample-containing surface flows through said membrane to said absorbent body, wherein said surfactant in said limited region permits the liquid sample to flow through said limited region at a faster rate than the liquid sample flowing through said peripheral area.

2. The analytical device of claim 1 wherein said concentration of surfactant within said limited region is at least two times higher than that of said area peripheral to said limited region.

3. The analytical device of claim 1 wherein said at least one surfactant is selected from the group consisting of amine alkylbenzene sulfonates, sodium N-oleyl-N-methyltaurate, sodium olefin (C14–C16) sulfonate, ammonium lauryl sulfates, octyl phenoxy polyethoxy ethanols, polyethylene glycols having molecular weight less than about 8,000 dimethicone copolyols, and cholic acid surfactants and salts of said cholic acid surfactants.

4. The analytical device of claim 1 wherein said at least one surfactant is an anionic surfactant having a molecular weight of less than about 1,000.

5. The analytical device of claim 1 wherein said surfactant comprises a cholic acid surfactant or salt thereof.

6. The analytical device of claim 1 wherein said surfactant-containing solution comprises about 0.2% to about 15.0% surfactant.

7. The analytical device of claim 6 wherein said surfactant requires at least 10 minutes of stirring at room temperature to prepare a 10% solution in a solvent.

8. The analytical device of claim 6 wherein said surfactant-containing solution is substantially protein-free, and wherein said reaction membrane has not been blocked with a protein-containing solution.

9. The analytical device of claim 1 wherein said surfactant-containing solution comprises about 0.2 to about 5.0% surfactant.

10. The analytical device of claim 1 wherein said surfactant-containing solution comprises about 0.5 to about 2.0% surfactant.

11. The analytical device of claim 1 wherein said limited region of said exposed sample-contacting surface has been pre-treated with said surfactant-containing solution and wherein portions of said exposed sample-contacting surface peripheral to said limited region have not been pre-treated with said surfactant-containing solution.

12. The analytical device of claim 11 wherein said surfactant-containing solution comprises about 2.5% to about 15.0% surfactant.

13. The analytical device of claim 11 wherein said surfactant-containing solution comprises about 4.0% to about 12.0% surfactant.

14. The analytical device of claim 1 wherein HIV antigen is located at said receptor area.

15. The analytical device of claim 1 having more than one receptor area.

16. The analytical device of claim 1 wherein said reaction membrane comprises nitrocellulose.

17. The analytical device of claim 1 in which said limited region is free of a light emitting labeled compound.

18. The analytical device of claim 1 in which said surfactant is not reactive with a chemiluminescent compound to enhance its chemiluminescence.

19. The analytical device of claim 1 in which said reaction membrane is free of said target substance.

* * * * *